(12) United States Patent
Mizukami

(10) Patent No.: US 7,026,836 B2
(45) Date of Patent: Apr. 11, 2006

(54) METHOD AND APPARATUS FOR TESTING A WAFER USING A LASER BEAM WAVELENGTH THAT DOES NOT GENERATE PHOTOVOLTAGE BY EXCITATION

(75) Inventor: Hirotaka Mizukami, Kanagawa-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/053,897

(22) Filed: Feb. 10, 2005

(65) Prior Publication Data

US 2005/0179460 A1 Aug. 18, 2005

(30) Foreign Application Priority Data

Feb. 17, 2004 (JP) .............................. 2004-039863

(51) Int. Cl.
*G01R 31/26* (2006.01)
(52) U.S. Cl. ....................... 324/765; 324/751
(58) Field of Classification Search ..................... None
See application file for complete search history.

(56) References Cited

U.S. PATENT DOCUMENTS

| 5,365,034 | A | * | 11/1994 | Kawamura et al. | .... 219/121.83 |
| 5,804,980 | A | * | 9/1998 | Nikawa | ....................... 324/752 |
| 6,078,183 | A | * | 6/2000 | Cole, Jr. | ...................... 324/752 |
| 6,407,558 | B1 | * | 6/2002 | Shabde et al. | .............. 324/750 |
| 6,545,500 | B1 | * | 4/2003 | Field | ........................... 324/770 |

\* cited by examiner

*Primary Examiner*—Paresh Patel
*Assistant Examiner*—Richard Isla-Rodas
(74) *Attorney, Agent, or Firm*—Fitzpatrick, Cella, Harper & Scinto

(57) ABSTRACT

Provided is a semiconductor device wafer testing method is provided, including: irradiating a wafer on which a semiconductor device chip is integrated with a quantum beam, and shifting an irradiation position thereof while detecting one of a thermoelectric current and a thermoelectric voltage which are generated in the wafer; and determining whether or not the detected one of the thermoelectric current and the thermoelectric voltage exceeds a threshold and storing as defect position address information an irradiation position of the quantum beam on the wafer when the detected one of the thermoelectric current and the thermoelectric voltage exceeds the threshold.

6 Claims, 3 Drawing Sheets

METHOD AND APPARATUS FOR TESTING A WAFER USING A LASER BEAM WAVELENGTH THAT DOES NOT GENERATE PHOTOVOLTAGE BY EXCITATION

BACKGROUND OF THE INVENTION

1. Field of the Invention

The present invention relates to a semiconductor device chip wafer testing method and apparatus for detecting a crystal defect in a wafer stage during a process for manufacturing a semiconductor device, in particular, a compound semiconductor laser diode or a light emitting diode.

2. Related Background Art

In a general method of manufacturing a compound semiconductor laser diode device, plural kinds of compound semiconductor layers are successively formed through crystal growth on a predetermined substrate and stacked to manufacture an epitaxial wafer. Next, in order to obtain a stripe structure serving as a resonator, the wafer is etched to remove a part thereof. After a film formation process including impurity diffusion, crystal growth, and electrode formation is completed, the wafer is cleaved and diced into individual chips (chip dicing).

There has been known that a crystal defect called "dislocation" occurs in the above-mentioned process for manufacturing the wafer for the compound semiconductor laser diode device. In general, a compound semiconductor substrate includes a crystal defect. Therefore, when epitaxial growth is made on the compound semiconductor substrate, the defect grows in a stacked compound semiconductor layer. Even at a position in which the crystal defect does not exist on a surface of the substrate, a new crystal defect is caused due to an impurity or the like which is deposited on the surface of a layer of compound semiconductor layers successively stacked during a crystal growth process and then grows. When the crystal defect exists in a stripe structural portion, a dark line defect (DLD) grows from a crystal defect portion by energization during operation. Therefore, light power reduces and the life of the compound semiconductor laser diode device shortens, so that the reliability of the device significantly reduces.

Thus, according to a conventional technique, a testing method of discriminating a deteriorated product having a short life through aging which means that a completed product of the compound semiconductor laser diode device is operated for several hours to several tens of hours under a high-temperature environment is generally used in order to remove a defect element in which a crystal defect exists in the stripe structural portion. However, such an aging method causes an increase in manufacturing cost of the laser diode device. In addition, it is hard to detect all products having the crystal defect using only the aging method.

SUMMARY OF THE INVENTION

An object of the present invention is to provide a semiconductor device chip wafer testing method and apparatus which are capable of detecting a crystal defect in an inner portion of a semiconductor laser diode device in a wafer stage and improving test efficiency and throughput without reduction in mass productivity.

A semiconductor device wafer testing method according to the present invention includes: irradiating a wafer on which a semiconductor device chip is integrated with a quantum beam, and shifting an irradiation position thereof while detecting one of a thermoelectric current and a thermoelectric voltage which are generated in the wafer; and determining whether or not the detected one of the thermoelectric current and the thermoelectric voltage exceeds a threshold and storing as defect position address information an irradiation position of the quantum beam on the wafer when the detected one of the thermoelectric current and the thermoelectric voltage exceeds the threshold.

According to the structure, while the irradiation position of the quantum beam is shifted, that is, while scanning is performed, a defect position on the wafer is discriminated. Therefore, positional information of the defect position can be obtained as the defect position address information. This information can be used to remove a defective chip after chip dicing. At this time, the defect position is discriminated based on whether or not one of the thermoelectric current and the thermoelectric voltage exceeds the threshold, so that the discrimination does not require a long time. Thus, the defect discrimination can be performed during high-speed scanning.

A semiconductor device wafer testing apparatus according to the present invention includes: a mount on which a wafer in which a chip of a semiconductor device is integrated is set and which can hold the wafer; a quantum beam scanning device capable of irradiating the wafer set on the mount with a quantum beam and shifting an irradiation position thereof on the wafer; a thermoelectric detecting portion for measuring one of a thermoelectric current and a thermoelectric voltage which are generated in the semiconductor device and determining whether or not the measured one of the thermoelectric current and the thermoelectric voltage exceeds a threshold; a defect position address memory; and a defect position address discriminating portion for measuring an irradiation position of the quantum beam from the quantum beam scanning apparatus when the thermoelectric detecting portion determines that the measured one of the thermoelectric current and the thermoelectric voltage exceeds the threshold, and causing the defect position address memory to store the measured irradiation position as defect position address information.

According to the structure, while high-speed scanning is performed by the quantum beam scanning apparatus, a defect position on the wafer is discriminated by the defect position address discriminating portion and stored as the defect position address information in the defect position address memory. Thus, the defect position address information stored in the defect position address memory can be used to remove a defective chip after chip dicing.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

Figure 1:
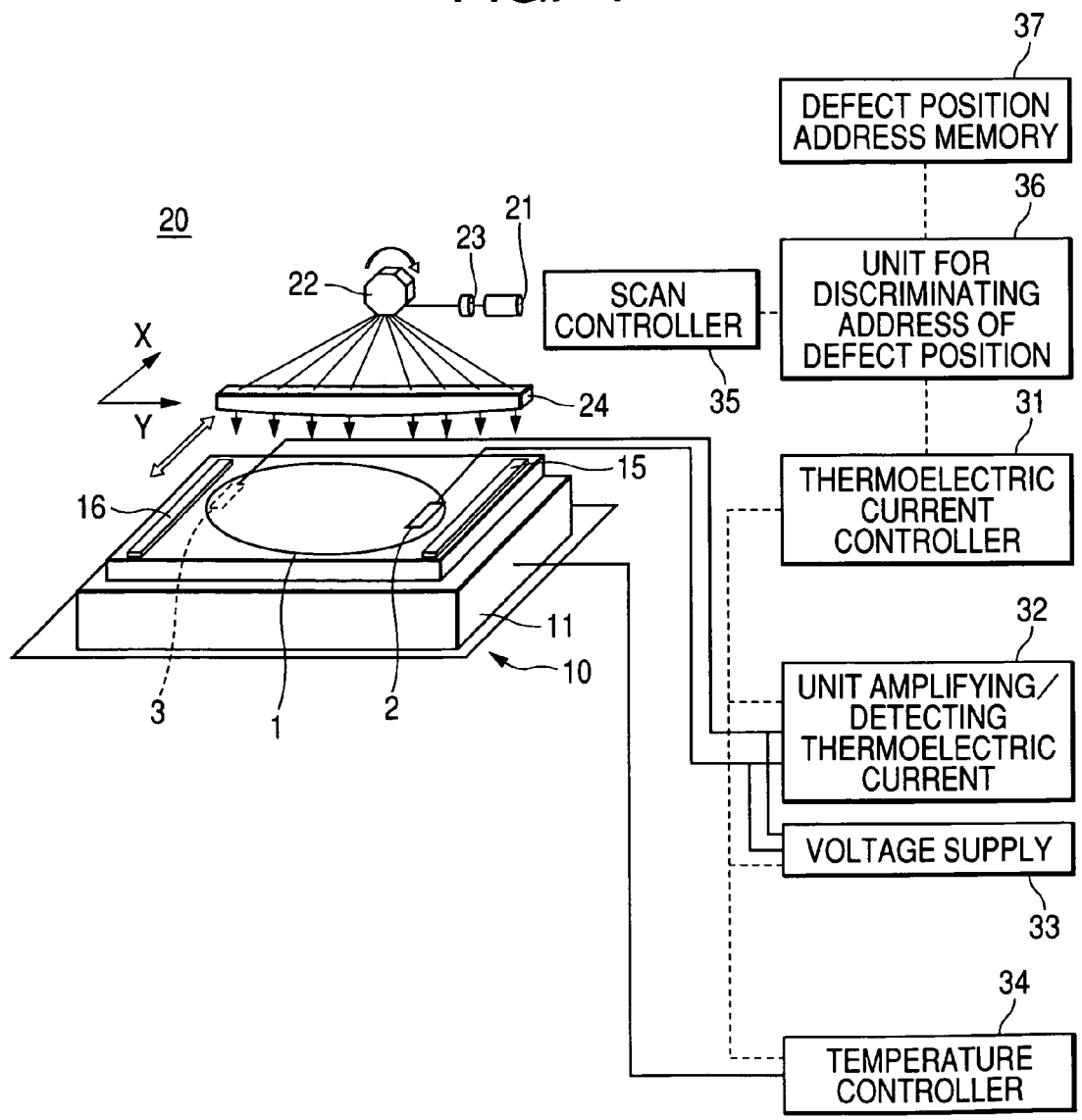
FIG. 1 is an entire structural diagram showing a semiconductor device chip wafer testing apparatus according to a first embodiment of the present invention.

FIG. 1 is an entire structural diagram showing a semiconductor device chip wafer testing apparatus according to a first embodiment of the present invention.

The semiconductor device chip wafer testing apparatus according to this embodiment includes a mount 10 on which a wafer 1 in which a compound laser diode chip, serving as a test object, is integrated is set and which holds the wafer 1. As shown in FIG. 1, the mount 10 has a size in which the wafer 1 having a general disk shape can be set.

Photo diodes (PDs) as described later are located on a sub-mount portion of the mount 10 on both sides of the set wafer 1 interposed therebetween as viewed in a scan direction (Y-direction in FIG. 1) of laser light scanned by the rotation of a polygon mirror 22. Each of the photo diodes is linearly extended in a direction (X-direction in FIG. 1) orthogonal to the scan direction. One of the photo diodes is a start position detection PD 15 operative to detect scan start timing of the laser light. The other photo diode is an end position detection PD 16 operative to detect scan end timing of the laser light. As described later, signals from the photo diodes are used to calculate a defect position address. Therefore, although not shown, the photo diodes are connected with a defect position address discriminating unit 36 as described later.

An upper electrode 2 and a lower electrode 3 are formed in advance on an upper surface and lower surface of the wafer 1, respectively. The upper electrode 2 and the lower electrode 3 are connected with an anode and cathode of the laser diode chip formed on the wafer 1, respectively. At this time, the upper electrode 2 and the lower electrode 3 are preferably provided on a region of the wafer 1 on which the laser diode chip is not formed. Even when the upper electrode 2 and the lower electrode 3 are provided on a region on which the laser diode chip is formed, as described later, at least an opening for exposing an upper portion of an oscillator of the laser diode chip is formed in the upper electrode 2 on the wafer 1 on which the laser diode chip is formed in order to prevent the irradiated laser light from blocking.

The upper electrode 2 and lower electrode 3 of the wafer 1 held on the mount 10 are connected with a thermoelectric current amplifying/detecting unit 32 and a voltage supply 33 through a probe and the like. The thermoelectric current amplifying/detecting unit 32 is operative to amplify the thermoelectric current generated between the upper electrode 2 and the lower electrode 3 and to determine whether or not the thermoelectric current is equal to or larger than a threshold. The voltage supply 33 is operative to supply a predetermined voltage between the upper electrode 2 and the lower electrode 3.

Although not shown in detail, a pipe into which a heating medium flows is provided in a stem portion 11 of the mount 10. A temperature controller 34 for controlling temperature of the wafer 1 set on the mount 10 is provided for a system that supplies or circulates the heating medium.

A laser light scanning apparatus (quantum beam scanning apparatus) 20 operative to scan the wafer 1 set on the mount 10 with laser light serving as a quantum beam is located above the mount 10. The laser light scanning apparatus 20 includes a laser light generating device (quantum beam generating device) 21 and an optical system for guiding laser light generated by the laser light generating device 21 onto the mount 10. The polygon mirror 22, which can be rotated by a rotation drive system (not shown), is provided in the optical system. A lens 23 for guiding irradiation light to a predetermined position on the polygon mirror 22 is provided on a light exit side of the laser light generating device 21. An fθ lens 24 extended in the horizontal direction, that is, a direction (Y-direction) perpendicular to a rotational axis (X-direction) of the polygon mirror 22 is provided below the polygon mirror 22. The fθ lens 24 is operative to guide light reflected by the polygon mirror 22 onto the mount 10. At this time, an optical system having a structure suitable to focus laser light as a minute spot on the surface of the wafer 1 held on the mount 10 is used as the optical system of the laser light scanning apparatus 20.

In the laser light scanning apparatus 20, while laser light is generated by the laser light generating device 21, the polygon mirror 22 is rotated clockwise as indicated by an arrow in FIG. 1 at predetermined constant rate. Therefore, an irradiation position of the laser light on the mount 10 is successively shifted from the right to the left in FIG. 1 along the Y-direction. Thus, scanning can be performed at high speed along a scan line extended in the Y-direction by using the laser light scanning apparatus 20 including the polygon mirror 22 which is located at a position on which the laser light generated by the laser light generating device 21 is incident and driven to rotate. Although not shown in detail, the laser light scanning apparatus 20 can be moved in the X-direction by a moving mechanism including a linear encoder, so that the scan line can be changed to the X-direction.

The thermoelectric current amplifying/detecting unit 32, the voltage supply 33, and the temperature controller 34 are connected with a thermoelectric current controller 31 that controls the operations of those. The operation of the laser light scanning apparatus 20 is controlled by a scan controller 35. According to the semiconductor device chip wafer testing apparatus in this embodiment, as described below in detail, a position on the wafer 1 in which an abnormal state such as a defect occurs, that is, a defect position address thereon is discriminated based on whether or not a thermoelectric current equal to or larger than a threshold is generated and a laser irradiation position at a time when the thermoelectric current is generated. The defect position address discriminating unit 36 that performs the discrimination of the defect position address and processing for storing the discriminated defect position address information is connected with the thermoelectric current controller 31 and the scan controller 35. The defect position address discriminating unit 36 is connected with a defect position address memory 37 for storing the defect position address information.

Figure 2:
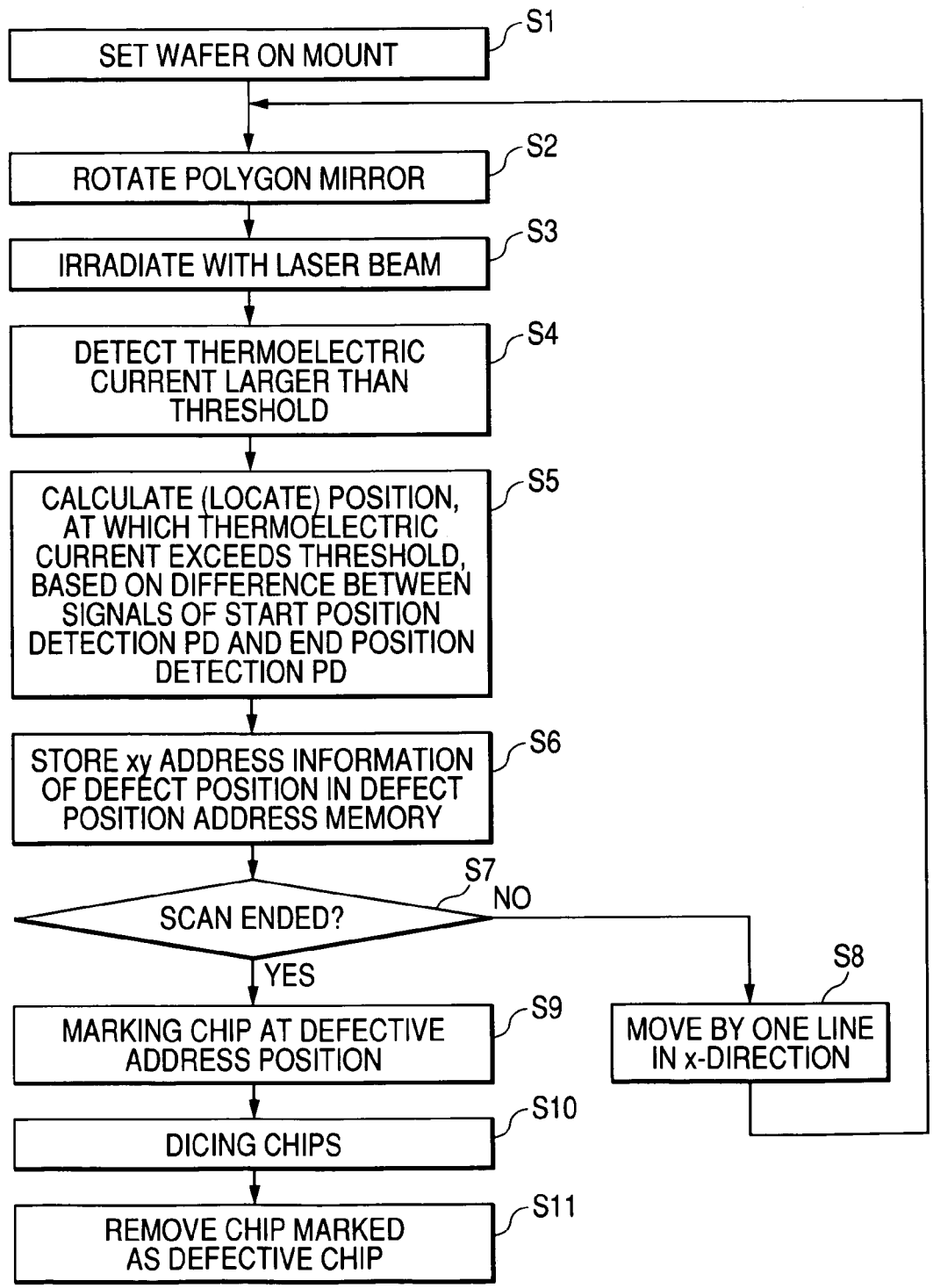
FIG. 2 is a schematic flow chart showing testing performed by the semiconductor device chip wafer testing apparatus shown in FIG. 1.

Next, a testing method according to this embodiment will be described with reference to a schematic flow chart shown in FIG. 2.

First, the wafer 1 is set on the mount 10 (Step S1). At this time, the wafer 1 is located such that a longitudinal direction of the oscillator of the laser diode chip formed on the wafer 1 becomes parallel to or perpendicular to the Y-direction which is the scan direction caused by the rotation of the polygon mirror 22. As described above, the voltage supply 33 and the thermoelectric current amplifying/detecting unit 32 are connected with each of the upper electrode 2 and lower electrode 3 of the wafer 1 through the probe and the like.

Next, the laser light scanning apparatus 20 is moved to a predetermined position on the wafer 1 by the moving mechanism and the polygon mirror 22 is rotated at constant rate (Step S2). Then, the laser light generating device 21 is activated to start laser light irradiation (Step S3).

Therefore, the wafer 1 is irradiated with laser light in a spot shape and the irradiation position is shifted in the Y-direction to perform scanning. When the laser light is emitted to a position on the wafer 1 in which an abnormal state such as a defect occurs due to the occurrence of dislocation or the like during scanning, thermoelectric power is produced by the Seebeck effect. A thermoelectric current resulting from the thermoelectric power flows from the upper electrode 2 and the lower electrode 3 into the thermoelectric current amplifying/detecting unit 32 and is amplified. Whether or not there is an abnormal portion is determined in accordance with whether or not a thermoelectric current exceeds the threshold (Step S4). At this time, the threshold for determining whether or not there is the abnormal portion is set in advance by a theoretical estimation or an experiment.

In the case of detection of the thermoelectric current, in order to prevent an optical beam induced current (OBIC) which is a photo-excitation current generated by irradiation with the laser light from becoming a noise, the irradiated laser light has energy lower than a band gap of the wafer 1 serving as an object to be observed, that is, a predetermined wavelength or more. In addition, the irradiated laser light has predetermined energy or more, that is, the predetermined wavelength or less so as to sufficiently transmit through the wafer 1. When the wavelength of the irradiated laser light is set as described above, the abnormal portion can be detected with high precision.

The application of a forward bias or backward bias to the wafer 1 at the time of irradiation with the laser light is effective to improve detection sensitivity of the abnormal portion using the Seebeck effect. Therefore, a predetermined voltage is applied from the voltage supply 33 to the wafer 1. In addition, producing efficiency of the thermoelectric current becomes maximal under a condition in which a temperature of the wafer 1 is a predetermined temperature, so that such control is similarly effective to improve the detection sensitivity of the abnormal portion. Therefore, the temperature control is performed by the temperature controller 34 during scanning. The reliability of testing can be improved by those operations.

When whether or not the generated thermoelectric current exceeds the threshold is determined, an amplified minute current is averaged by laser light staying times at respective scan points. In order to adequately average the amplified minute current, scanning is performed necessary times. The averaged minute current is converted into a voltage and subjected to A/D conversion. An accurate determination can be performed by those operations.

Figure 3:
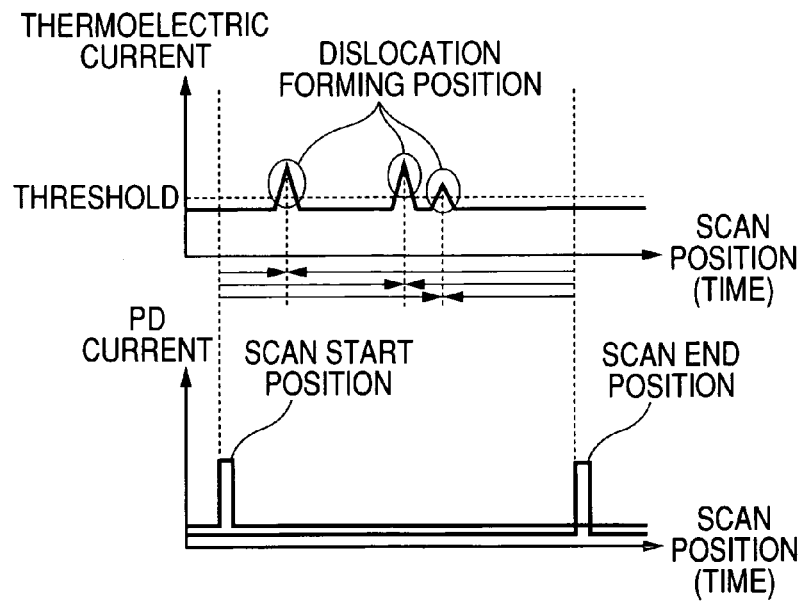
FIG. 3 is a schematic graph showing a measurement result of a thermoelectric current obtained by the semiconductor device chip wafer testing apparatus shown in FIG. 1.

Next, when the thermoelectric current that exceeds the threshold is detected, a Y-directional address of a region determined to be an abnormal portion is discriminated by the defect position address discriminating unit 36 (Step S5). The determination is performed by comparison between timing at which the thermoelectric current that exceeds the threshold is detected and timings at which laser light detection signals are generated by the start position detection PD 15 and the end position detection PD 16. FIG. 3 shows schematic graphs showing the determination. In FIG. 3, an upper graph shows a change in a detection value of the thermoelectric current with time during one scanning. A lower graph shows generation timing of signal currents from the photo diodes at the same times. During one scanning, a signal current is generated by the start position detection PD 15 at the time of scan start and a signal current is generated by the end position detection PD 16 at the time of scan end. Therefore, the Y-directional position (address) can be calculated from a difference between a generation time of the signal current from the start position detection PD 15 and a generation time of the thermoelectric current that exceeds the threshold and a difference between a generation time of the signal current from the end position detection PD 16 and the generation time of the thermoelectric current that exceeds the threshold.

Next, the calculated Y-directional address, that is, the Y-directional address of the position which is determined to be the defect position by the detection of the thermoelectric current that exceeds the threshold is stored as defect position address information in the defect position address memory 37 together with an X-directional address determined from a position of the laser light scanning apparatus 20 at the time of scanning (Step S6).

Scanning related to one scan line in the Y-direction is completed by the processes of Steps S2 to S6. Next, the laser light scanning apparatus 20 is moved to an adjacent scan line by one in the X-axis direction by the moving mechanism. Then, scanning related to one scan line in the Y-direction is similarly performed. Such operation is repeated until the entire surface of the wafer is completely scanned (Steps S7 and S8).

After the entire surface of the wafer is completely scanned, the wafer 1 is marked in ink or the like at the defective address position stored in the defect position address memory 37 (Step S9). After the wafer is diced into chips (Step S10), The marked chip is removed as a defective chip.

According to the semiconductor device chip wafer testing method in this embodiment as described above, the wafer 1 is irradiated with the laser light in the spot shape and the irradiation position is shifted at high speed. That is, the wafer 1 is scanned. During scanning, the process is performed in which the laser irradiation position at a time when the thermoelectric current equal to or larger than the threshold is generated is determined to be the abnormal portion. Therefore, it is possible to efficiently obtain the defect position address information which is position information of the abnormal portion on the wafer 1 at high speed. At this time, the defective chip can be discriminated by testing in the wafer stage, so that general aging in a conventional technique is unnecessary. That is, the defective chip can be removed from products after wafer dicing based on the obtained defect position address information.

As described above, according to the semiconductor device chip wafer testing method in this embodiment, the test efficiency and test throughput are high. Therefore, the semiconductor device chip wafer testing method is suitably used for a mass production process. Thus, the defective chip can be accurately removed without reduction in mass productivity to manufacture high quality products.

In this embodiment, the start position detection PD 15 and the end position detection PD 16, each of which is linearly extended in the X-direction are located. A structure extended in an arc shape along the edge of the disk-shaped wafer 1 may be used. A more compact structure may be used for the mount 10. For example, a structure capable of holding a wafer divided in advance by a suitable size and in suitable number, such as a structure in which a wafer is cut in a rectangular shape or a bar shape in each laser diode chip column on the mount 10 may be used. A structure in which a Peltier element is provided in the stem portion 11 may be used to adjust the temperature of the wafer 1 on the mount 10.

In this embodiment, the example in which the wafer 1 on which semiconductor laser diode devices are formed is tested is described. However, an object to be tested by the testing method of the present invention is not limited to this. In general, a wafer on which a semiconductor device chip is integrated can be tested as the object to be tested. As such an object to be tested, there is, for example, a wafer on which light emitting diodes serving as compound semiconductor devices are formed.

In this embodiment, the thermoelectric current amplifying/detecting unit 32 that amplifies the current generated by the thermoelectric power and determines whether or not the amplified current exceeds the threshold current is used as a thermoelectric power detecting unit that measures generated thermoelectric power and determines whether or not the measured thermoelectric power exceeds a predetermined value. A structure in which whether nor not the thermoelectric power exceeds the predetermined value is determined based on a generated voltage may be used.

In this embodiment, the example in which the scanning mechanism using the polygon mirror 22 to shift the irradiation position of the laser light, that is, to perform scanning is used for the quantum beam scanning apparatus is described. However, another scanning mechanism may be used. It is preferable to use a scanning mechanism capable of performing scanning at high speed in any case.

Figure 4:
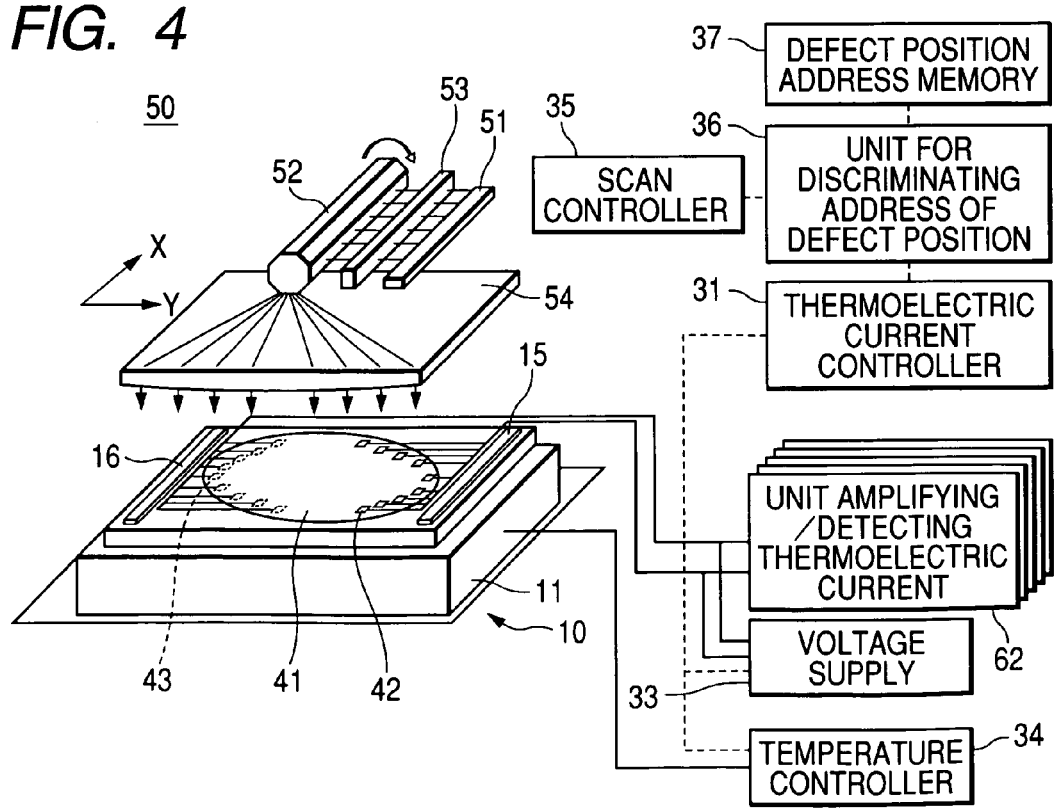
FIG. 4 is an entire structural diagram showing a semiconductor device chip wafer testing apparatus according to a second embodiment of the present invention.

Next, a second embodiment of the present invention will be described with reference to FIG. 4. FIG. 4 is an entire schematic structural diagram showing a semiconductor device chip wafer testing apparatus according to this embodiment. In FIG. 4, the same references are assigned to the same portions as those in the first embodiment and the detailed description is omitted here.

In this embodiment, a laser light scanning apparatus 50 includes a multi-beam laser light generating device 51 provided with a laser array. The multi-beam laser light generating device 51 can simultaneously generate a plurality of laser light beams arranged in the X-direction as a rotational axis direction of a polygon mirror 52. The polygon mirror 52, a lens 53, and an fθ lens 54 each have a predetermined size in the X-direction so as to be capable of simultaneously guiding the plurality of laser light beams. Therefore, it is possible to simultaneously scan a plurality of scan lines extended in a direction perpendicular to the rotational axis direction of the polygon mirror 52, that is, the Y-direction which is the horizontal direction.

With respect to a wafer 41 set on the mount 10, an upper electrode 42 and a lower electrode 43 are formed in advance for each of the plurality of scan lines. Although connections are simply shown in FIG. 4, the upper electrode 42 and the lower electrode 43 are connected with a separate thermoelectric current amplifying/detecting unit 62 for each of the scan lines. Therefore, the position at which the thermoelectric current that exceeds the threshold is generated, that is, the abnormal portion can be simultaneously detected for each of the scan lines.

As described above, according to this embodiment, the abnormal portions can be simultaneously detected for the plurality of scan lines. As a result, testing is more efficiently performed, so that the test efficiency and throughput can be further improved.

In this embodiment, the example in which the polygon mirror 52 extended along the arrangement of the laser array is used to perform scanning with the plurality of laser light beams is described. However, another scanning mechanism capable of shifting an irradiation position of each of the laser light beams, that is, of performing scanning with each of the laser light beams may be used. When simultaneous scanning is performed using the plurality of laser light beams in any case, it is possible to obtain an operation in which the test efficiency is improved.

The present invention is not limited to the case of testing by using laser light, and is effective for the case of testing by using a quantum beam such as an electron beam or an ion beam.

According to the present invention, the abnormal portion including the crystal defect is detected in not a completed product state but a wafer stage and the position thereof is stored as the defect position address information. Therefore, of chips serving as completed products, a defective chip can be removed based on the stored defect position address information. Thus, it is unnecessary to perform general aging in a conventional technique on completed products, so that a manufacturing cost can be reduced.

According to the present invention, the defect position address on the wafer can be discriminated during high-speed scanning. In addition, the test efficiency and throughput can be significantly improved as compared with a conventional technique in which the defect position address is discriminated by image processing. Thus, a technique of the present invention can be suitably applied to a mass production process.

This application claims priority from Japanese Patent Application No. 2004-039863 filed Feb. 17, 2004, which is hereby incorporated by reference herein.

What is claimed is:

1. A semiconductor device wafer testing method, comprising:
    irradiating a wafer on which a semiconductor device chip is integrated with a laser beam having a wavelength that is transmitted through a crystal portion of the wafer and does not generate photovoltage by excitation, and shifting an irradiation position thereof while detecting one of a thermoelectric current and a thermoelectric voltage which are generated in the wafer; and
    determining whether or not the detected one of the thermoelectric current and the thermoelectric voltage exceeds a threshold, and storing as defect position address information an irradiation position of the laser beam on the wafer when the detected one of the thermoelectric current and the thermoelectric voltage exceeds the threshold.

2. A semiconductor device wafer testing method according to claim 1, wherein the irradiation position on the wafer is shifted by irradiation of the laser light on a polygon mirror rotating.

3. A semiconductor device wafer testing method according to claim 1, wherein the wafer is simultaneously irradiated with a plurality of laser beams, irradiation positions of the quantum beams are simultaneously shifted, and thermoelectric power generated by irradiation with the laser beams are simultaneously detected.

4. A semiconductor device wafer testing apparatus, comprising:

a mount on which a wafer in which a chip of a semiconductor device is integrated is set and which can hold the wafer;

a laser beam scanning device capable of irradiating the wafer set on the mount with a laser beam having a wavelength that is transmitted through a crystal portion of the wafer and does not generate electromotive force by excitation and shifting an irradiation position thereof on the wafer;

a thermoelectric detecting portion for measuring one of a thermoelectric current and a thermoelectric voltage which are generated in the semiconductor device and determining whether or not the measured one of the thermoelectric current and the thermoelectric voltage exceeds a threshold;

a defect position address memory; and a defect position address discriminating portion for measuring an irradiation position of the laser beam from the laser beam scanning apparatus when the thermoelectric detecting portion determines that the measured one of the thermoelectric current and the thermoelectric voltage exceeds the threshold, and causing the defect position address memory to store the measured irradiation position as defect position address information.

5. A semiconductor device wafer testing apparatus according to claim 4, wherein the laser beam scanning device comprises a laser beam generating device for generating the laser beam and a polygon mirror which is located at a position where the laser beam generated by the laser beam generating device is incident and rotated.

6. A semiconductor device wafer testing apparatus according to claim 4, wherein the laser beam scanning apparatus comprises a laser beam generating device capable of simultaneously generating a plurality of quantum beams.

* * * * *

UNITED STATES PATENT AND TRADEMARK OFFICE
CERTIFICATE OF CORRECTION

PATENT NO. : 7,026,836 B2
APPLICATION NO. : 11/053897
DATED : April 11, 2006
INVENTOR(S) : Hirotaka Mizukami It is certified that error appears in the above-identified patent and that said Letters Patent is hereby corrected as shown below:

TITLE PAGE:
(75) Inventor: "Kanagawa-ken" should read -- Yokohama --; and
(57) ABSTRACT "Provided is a" should read -- A --.

COLUMN 1:
Line 26, "There" should read -- It --.

Signed and Sealed this

Twenty-sixth Day of December, 2006

JON W. DUDAS
*Director of the United States Patent and Trademark Office*